United States Patent
Matsue et al.

(10) Patent No.: US 10,037,405 B2
(45) Date of Patent: Jul. 31, 2018

(54) MEDICAL IMAGE GENERATION APPARATUS, MEDICAL IMAGE STORAGE APPARATUS, MEDICAL IMAGE DISPLAY APPARATUS, AND MEDICAL IMAGE DISPLAY SYSTEM

(75) Inventors: Kenji Matsue, Nasushiobara (JP); Kenichi Niwa, Otawara (JP)

(73) Assignees: KABUSHIKI KAISHA TOSHIBA, Tokyo (JP); TOSHIBA MEDICAL SYSTEMS CORPORATION, Otawara-shi (JP)

( * ) Notice: Subject to any disclaimer, the term of this patent is extended or adjusted under 35 U.S.C. 154(b) by 1664 days.

(21) Appl. No.: 12/626,765

(22) Filed: Nov. 27, 2009

(65) Prior Publication Data

US 2010/0128943 A1    May 27, 2010

(30) Foreign Application Priority Data

Nov. 27, 2008 (JP) ................... 2008-302310
Nov. 10, 2009 (JP) ................... 2009-257220

(51) Int. Cl.
| | |
|---|---|
| G06Q 50/00 | (2012.01) |
| G06F 19/00 | (2018.01) |
| A61B 1/00 | (2006.01) |
| G06Q 10/00 | (2012.01) |
| G16H 30/40 | (2018.01) |

(52) U.S. Cl.
CPC ........ *G06F 19/321* (2013.01); *A61B 1/00009* (2013.01); *G16H 30/40* (2018.01)

(58) Field of Classification Search
CPC ............ G06T 7/0012; G06T 7/0083; G06T 2207/30004; G06T 7/0081; G06F 19/321
USPC ........................................................ 382/128
See application file for complete search history.

(56) References Cited

U.S. PATENT DOCUMENTS

| | | | |
|---|---|---|---|
| 6,608,628 B1 * | 8/2003 | Ross et al. .................... | 345/619 |
| 2005/0010445 A1 * | 1/2005 | Krishnan et al. ................ | 705/2 |

FOREIGN PATENT DOCUMENTS

| | | |
|---|---|---|
| JP | 2005-184377 | 7/2005 |
| JP | 2008-148849 | 7/2008 |

* cited by examiner

*Primary Examiner* — Tran N Nguyen
(74) *Attorney, Agent, or Firm* — Oblon, McClelland, Maier & Neustadt, L.L.P.

(57) ABSTRACT

A medical image generation apparatus including: a 4D image data generation unit generating 4D image data composed of a plurality of 3D image data blocks each having information indicating a number in chronological order of the 3D image data blocks using image information acquired by taking images of an object; and an image generation unit generating movie data composed of a plurality of 2D image data blocks generated from the plurality of 3D image data blocks constituting the four-dimensional image data and generating relevant information associating each of the two-dimensional image data blocks constituting the movie data with one of the 3D image data blocks which is the source of the 2D image data block.

4 Claims, 11 Drawing Sheets

MEDICAL IMAGE GENERATION APPARATUS, MEDICAL IMAGE STORAGE APPARATUS, MEDICAL IMAGE DISPLAY APPARATUS, AND MEDICAL IMAGE DISPLAY SYSTEM

CROSS REFERENCE TO RELATED APPLICATIONS

This application is based upon and claims the benefit of priority from prior Japanese Patent Application 2008-302310 filed on Nov. 27, 2008 and Japanese Patent Application 2009-257220 filed on Nov. 10, 2009 the entire contents of which are incorporated by reference herein.

BACKGROUND OF THE INVENTION

1. Field of the Invention

The present invention relates to a medical image generation apparatus, a medical image storage apparatus, a medial image display apparatus, and a medial image display system which allow the medical image display apparatus to display an medical image requested by an operator regardless of the performance of the medical image display apparatus by processing internal images of an object taken by the image generator.

2. Description of the Related Art

In recent years, medical diagnostic imaging apparatuses which collect internal information of an object and make internal images of the object based on the collected information to generate a medical image are used. Examples of such medical diagnostic imaging apparatuses are X-ray computed tomography (CT) apparatuses, magnetic resonance imaging (MRI) apparatuses, and the like. The generated medical images are displayed on a medical image display apparatus connected to the medical diagnostic imaging apparatus through a network.

As for these medical images, for example, a plurality of three-dimensional (hereinafter, properly referred to as 3D) data blocks are read in chronological order and are subjected to multi-planar reconstruction (MPR) or volume rendering by the medical image display apparatus. The obtained MPR images, 3D data images, or four-dimensional (hereinafter, also properly referred to as 4D) data are displayed.

However, it is difficult in some cases to easily know temporal changes of a portion (a site of interest) included in the 3D data. The invention disclosed in Japanese Patent Laid-open Publication No. 2008-148849 therefore proposes a medical diagnostic imaging apparatus which allows such temporal changes in a site of interest concerning a particular part to be known on a screen.

However, the invention disclosed in above Japanese Patent Laid-open Publication No. 2008-148849 does not consider the following point.

Specifically, even if 4D image data is generated, for example, based on data of images taken by the medical diagnostic imaging apparatus, there is a possibility that the generated 4D image data cannot be displayed by the medical image display apparatus connected to the network.

The amount of normal 4D image data is huge. Accordingly, even though a doctor tries to display 4D image data on the medical image display apparatus during an examination, the 4D image data cannot be displayed in some cases because of inadequate performance of the medical image display apparatus such as memory shortage thereof.

There is no point in not using or not being capable of using the generated 4D image. In addition, the places where the 4D images can be accessed are limited depending on the performance of the display apparatus such as the capability of processing 4D images or provision of software capable of reproducing 4D images. This can reduce the effective opportunities for the doctor to let the patient understand the symptoms.

On the other hand, instead of displaying 4D image data, it is possible to read and display only 3D image data blocks in chronological order. In this case, it is necessary to specify and display a 3D image data block of interest which is requested by an operator from a plurality of 3D image data blocks arranged in a number of time series. However, specifying the 3D image data block of interest is very complicated and cannot be easily conducted in many cases.

The present invention is made to solve the aforementioned problems, and an object of the present invention is to provide a medical image generation apparatus, a medical image storage apparatus, a medical image display apparatus, and a medical image display system which enable displaying a large amount of image data with a simple operation regardless of the performance of the display apparatus.

BRIEF SUMMARY OF THE INVENTION

A first aspect of the present invention is a medical image generation apparatus including: a four-dimensional image data generation unit generating four-dimensional image data composed of a plurality of three-dimensional image data blocks each having information indicating a number in chronological order of the three-dimensional image data blocks by using image information acquired by taking images of an object; and an image generation unit generating movie data composed of a plurality of two-dimensional image data blocks generated from the plurality of three-dimensional image data blocks constituting the four-dimensional image data and generating relevant information associating each of the two-dimensional image data blocks constituting the movie data with one of the three-dimensional image data blocks which is a source of the block of two-dimensional image data.

A second aspect of the present invention is a medical image storage apparatus including: a memory unit storing four-dimensional image data composed of a plurality of three-dimensional image data blocks each having information indicating a number in chronological order of the three-dimensional image data blocks; and an image generation unit generating movie data composed of a plurality of two-dimensional image data blocks generated from the plurality of three-dimensional image data blocks constituting the four-dimensional image data and generating relevant information associating each of the two-dimensional image data blocks constituting the movie data with one of the three-dimensional image data blocks which is a source of the two-dimensional image data block.

A third aspect of the present invention is a medical image display apparatus including: a display unit displaying an image; a display controller causing movie data on the display unit; a specification unit specifying two-dimensional image data constituting the movie data displayed on the display unit; and a processing unit acquiring three-dimensional image data based on relevant information for reading the three-dimensional image data from which the two-dimensional image data specified by the specification unit is generated.

A fourth aspect of the present invention is a medical image display system including: a four-dimensional image data generation unit generating four-dimensional image data composed of a plurality of three-dimensional image data blocks each having a number in chronological order of the three-dimensional image data blocks using image information acquired by taking images of an object; an image generation unit generating movie data composed of a plurality of two-dimensional image data blocks generated from the three-dimensional image data blocks constituting the four-dimensional image data and generating relevant information associating each of the two-dimensional image data blocks with one of the three dimensional image data blocks which is a source of the two-dimensional image data block; a display unit displaying an image; a display controller causing the movie data to be displayed on the display unit; a specification unit specifying one of the two-dimensional image data blocks constituting the movie data displayed on the display unit; and a processing unit acquiring the three-dimensional image data based on the relevant information.

BRIEF DESCRIPTION OF THE SEVERAL DRAWINGS

SUMMARY OF THE INVENTION

Detailed Description of the Invention

Hereinafter, embodiments of the present invention will be described in detail with reference to the drawings.

First Embodiment

Figure 1:
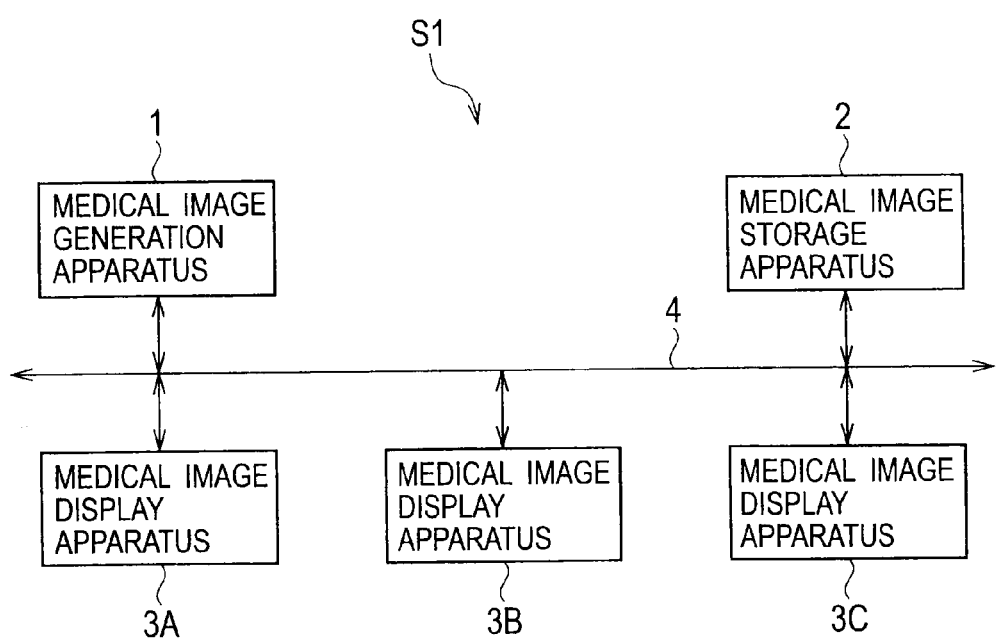
FIG. 1 is a block diagram showing an entire configuration of an image display system according to an embodiment of the present invention.

FIG. 1 is a block diagram showing the entire configuration of an image display system S1 according to the embodiment of the present invention. The image display system S1 includes a medical image generation apparatus 1, a medical image storage apparatus 2, and medical image display apparatuses 3A to 3C, which are connected to a network 4. The medical image generation apparatus 1 generates a plurality of time-series 3D image data blocks using image information acquired by taking images of an object and generates 2D movie data from the plurality of time-series 3D image data blocks. The medical image storage apparatus 2 stores the image data and movie data generated by the medical image generation apparatus 1. The medical image display apparatus 3 can display the movie data generated by the medical image generation apparatus 1. The plurality of time-series 3D image data blocks each have information indicating a number in chronological order, for example such as shooting time, as accompanying information. Such accompanying information may be just numerals indicating numbers in chronological order instead of time information.

In the image display system S1 shown in FIG. 1, the three medical image display apparatuses 3A to 3C (hereinafter, these plurality of medical image display apparatuses are properly indicated as the medical image display apparatus 3 collectively) are connected to the network 4. The number of the medical image display apparatuses connected to the network 4 can be one or more. Moreover, the medical image display apparatus 3 needs to at least have adequate performance enough to display 3D image data and is not necessary to have an ability to reproduce a plurality of time-series 3D image data blocks, that is, 4D image data.

Furthermore, the medical image generation apparatus 1 according to the first embodiment of the present invention includes functions of taking images of the object, collecting internal information of the object, and generating image data and movie data for display in the medical image display apparatus 3 based on the collected internal information of the object. These functions may be separately provided for different medical image generation apparatuses, which respectively perform image shooting and the data generation.

[Configuration and Function of Medical Image Generation Apparatus]

Next, among the apparatuses constituting the image display system S1, first, the configuration and functions of the medical image generation apparatus 1 is described.

Figure 2:
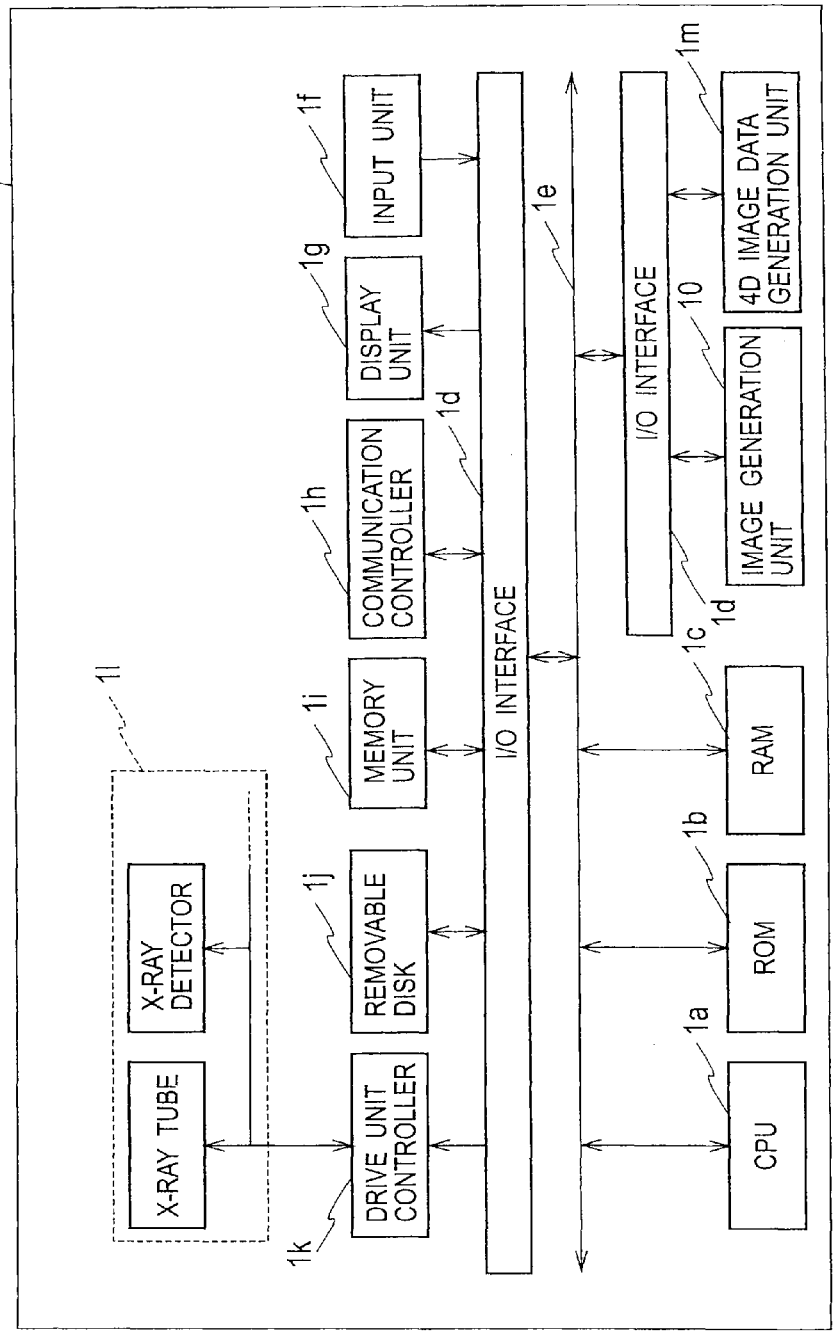
FIG. 2 is a block diagram showing the internal configuration of a medical image generation apparatus according to a first embodiment of the present invention.

FIG. 2 is a block diagram showing the internal configuration of the medical image generation apparatus 1 according to the first embodiment of the present invention. As the medical image generation apparatus, there are various types of apparatuses such as the aforementioned MRI apparatuses. In the embodiments of the present invention, the following description is given taking an X-ray CT apparatus as an example of the medical image generation apparatus 1.

The medical image generation apparatus 1 includes a central processing unit (CPU) 1a, a read only memory (ROM) 1b, a random access memory (RAM) 1c, and an I/O (I/O) interface 1d, which are connected to each other through a bus 1e. The I/O interface 1d is connected to an input unit 1f, a display unit 1g, a communication controller 1h, a memory unit 1i, a removable disk 1j, and a drive unit controller 1k. The drive unit controller 1k controls a drive unit 1l. The drive unit 1l includes an X-ray tube constituting the X-ray CT apparatus, an X-ray detector which receive X-rays, and the like, for example. Moreover, the I/O interface 1e is also connected to a 4D image data generation unit 1m and an image generation unit 10 through an I/O interface 1d.

The CPU 1a reads a boot program to boot up the medical image generation apparatus 1 from the ROM 1b based on an input signal from the input unit 1f, executes the same, and loads various types of operating systems stored in a memory unit 1i. The CPU 1a controls various devices based on input signals received from other external devices not shown in FIG. 1 through the input unit 1f or I/O interface 1d. Moreover, the CPU 1a loads programs and data stored in the RAM 1c, memory unit 1i, and the like onto the RAM 1c. The CPU 1a also serves as a processing unit implementing a series of processes including image generation, data calculation and processing, and the like based on commands of the programs read from the RAM 1c.

The input unit 1f is composed of input devices such as a keyboard and dials through which an operator (for example, a doctor or a laboratory technician) of the medical image generation apparatus 1 inputs various operations. The input unit 1f generates the input signal based on the operation by the operator and sends the same to the CPU 1a through the bus 1e. The medical image generation apparatus 1 is provided with a dedicated operating panel in addition to the keyboard and the like. The operator can perform operations for an operating screen through an input device on the operating panel.

The display unit 1g is a liquid crystal display, for example. The display unit 1g receives an output signal from the CPU 1a through the bus 1e and displays, for example, images necessary for setting various conditions at taking and processing images, processing results of the CPU 1a, and the like.

The communication controller 1h is a LAN card, a modem, or the like and allows the medical image generation apparatus 1 to be connected to a communication network such as the Internet and LAN. Data exchanged with the communication network through the communication controller 1h is exchanged with CPU 1a through the I/O interface 1d and bus 1e as input and output signals.

The memory unit 1i is composed of a semiconductor or a magnetic disk and stores programs executed by the CPU 1a and data.

The removable disk 1j is an optical or flexible disk. Signals read and written into the removable disk 1j by a disk drive are exchanged with the CPU 1a through the I/O interface 1d and bus 1e.

The 4D image data generation unit 1m collects volume data concerning internal information of the object from an electric signal generated by the X-ray detector detecting X-rays which are projected from the X-ray tube onto the object and transmitted through the object. The 4D image data generation unit 1m generates 3D image data blocks based on the volume data, organizes these 3D image data blocks in chronological order, and generates the 4D image data based on the plurality of 3D image data blocks.

The image generation unit 10 is connected to the I/O interface 1d and generates 2D movie data based on the 4D image data generated by the 4D image data generation unit 1m. The 2D image data is image data in which pixels corresponding to a two-dimensional space are arranged, and the 3D image data is image data in which pixels corresponding to a three-dimensional space (pixels corresponding to three spatial axes) are arranged.

In the first embodiment of the present invention, description is given of an example where the image generation unit 10 is mounted on the medical image generation apparatus 1 below. The image generation unit 10 may be configured to be provided independently of the medical image generation apparatus 1 and be connected to the medical image generation apparatus 1 through the network 4. In this case, the image generation unit 10 may be used in combination with various types of management systems built in a medical institution such as a hospital information system (HIS), a radiological information system (RIS), and a picture archiving communication system (PACS).

Examples of the network 4 are a local area network (LAN), the Internet, and the like. The communication standard used in the network 4 may be any standard such as Digital Imaging and Communication in Medicine (DICOM).

In the embodiment of the present invention, the image generation unit 10 carries out the image processing. However, the image processing can be carried out by using an image generation program stored in the memory unit 1i or removable disk 1j instead of the image generation unit 10. In this case, the program stored in these devices is read and executed by the CPU 1a, thus mounting the image generation unit onto the medical image generation apparatus 1.

Figure 3:
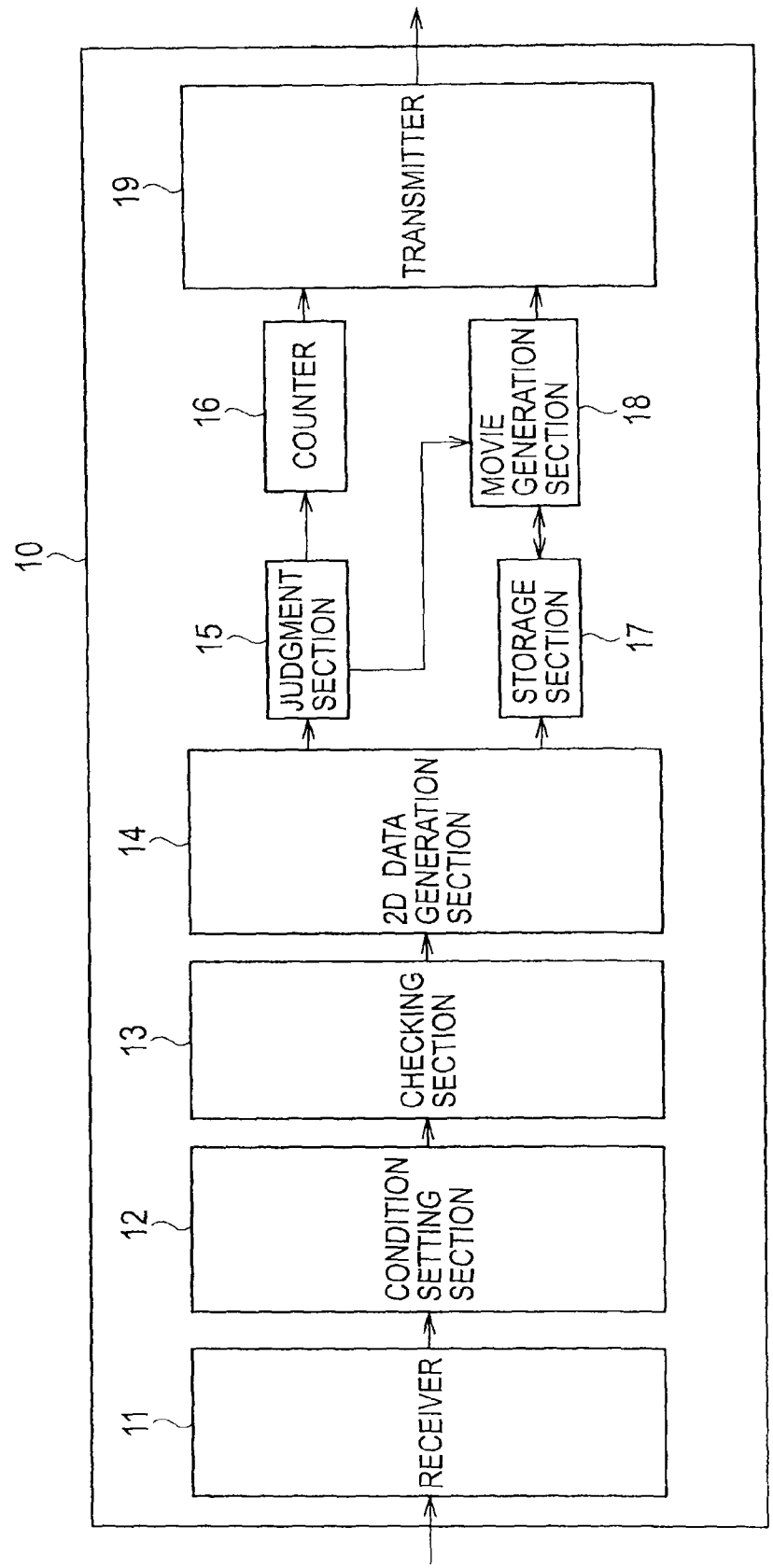
FIG. 3 is a block diagram showing the internal configuration of an image generation unit of the medical image generation apparatus.

FIG. 3 is a block diagram showing the entire internal configuration of the image generation unit 10 in the embodiment of the present invention. The image generation unit 10 generates 2D movie data from the 4D image data generated by the 4D image data generation unit 1m. The image generation unit 10 is composed of a receiver 11, a condition setting section 12, a checking section 13, a 2D data generation section 14, a judgment section 15, a counter 16, a storage section 17, a moving picture generation section 18, and a transmitter 19.

The condition setting section 12 sets conditions on how to display the 4D image data using the 4D image data, that is, how to display the same in the medical image display apparatus 3. As described above, the 4D image data is generated by the 4D image data generation unit 1m based on X-ray CT images taken by the medical image generation apparatus 1.

The checking section 13 identifies the 3D image data blocks constituting the 4D image data which is the source of the 2D movie data to be generated. The 2D data generation section 14 generates the 2D image data for preparation of generating the movie data.

After the 2D image data is generated by the 2D data generation section 14, the judgment section 15 judges whether the 2D image data is generated from all the 3D image data blocks. The counter 16 counts the number in chronological order of the 3D image data blocks. The generated 2D image data is stored in the storage section 17. The movie generation section 18 generates the 2D movie data from the 2D image data based on an instruction from the judgment section 15.

Figure 4:
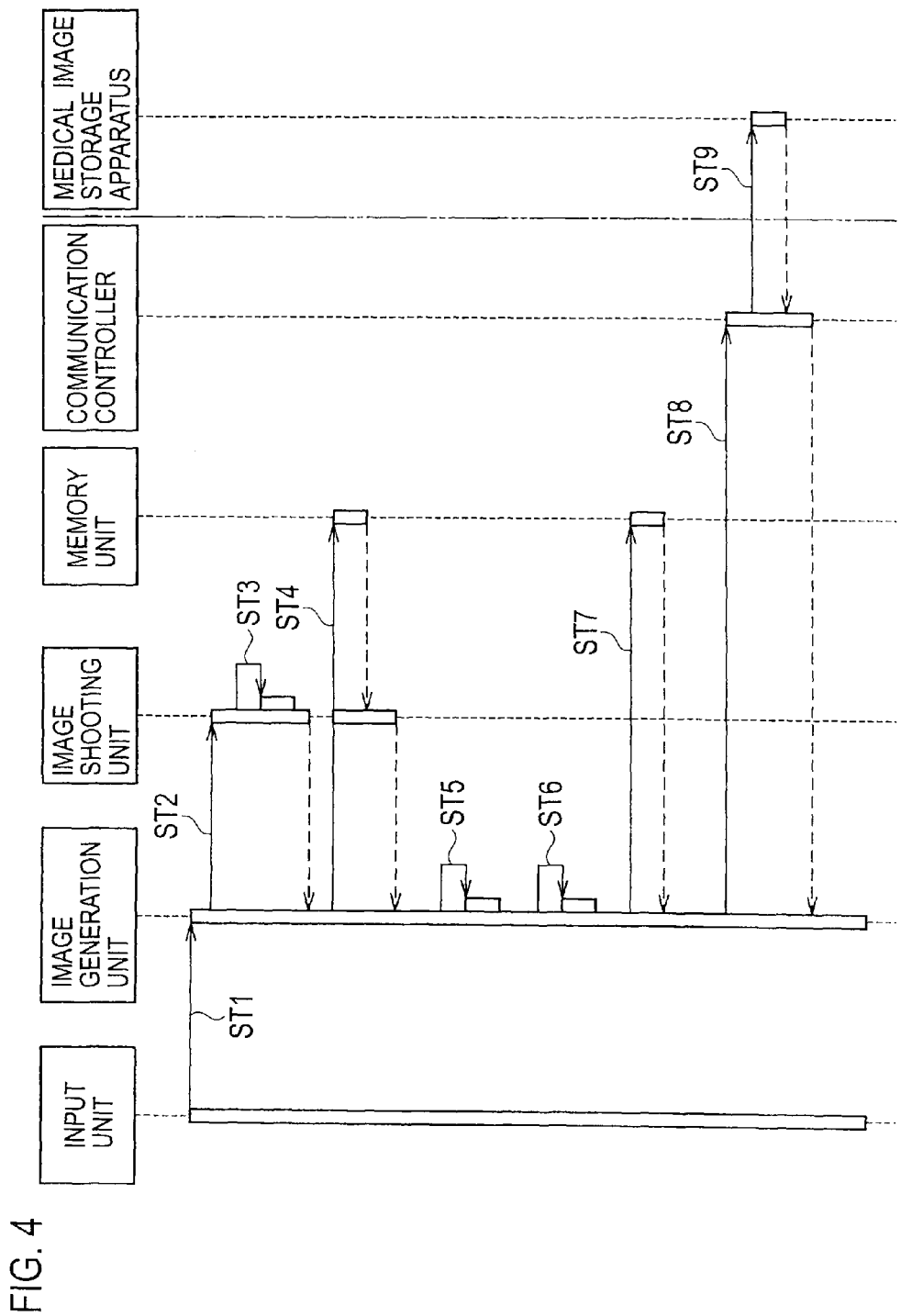
FIG. 4 is a sequence diagram showing a flow of generating 4D image data based on scanning data taken by the medical image generation apparatus and then generating 2D movie data from the 4D image data together with operations of functions of the medical image generation apparatus.
Figure 5:
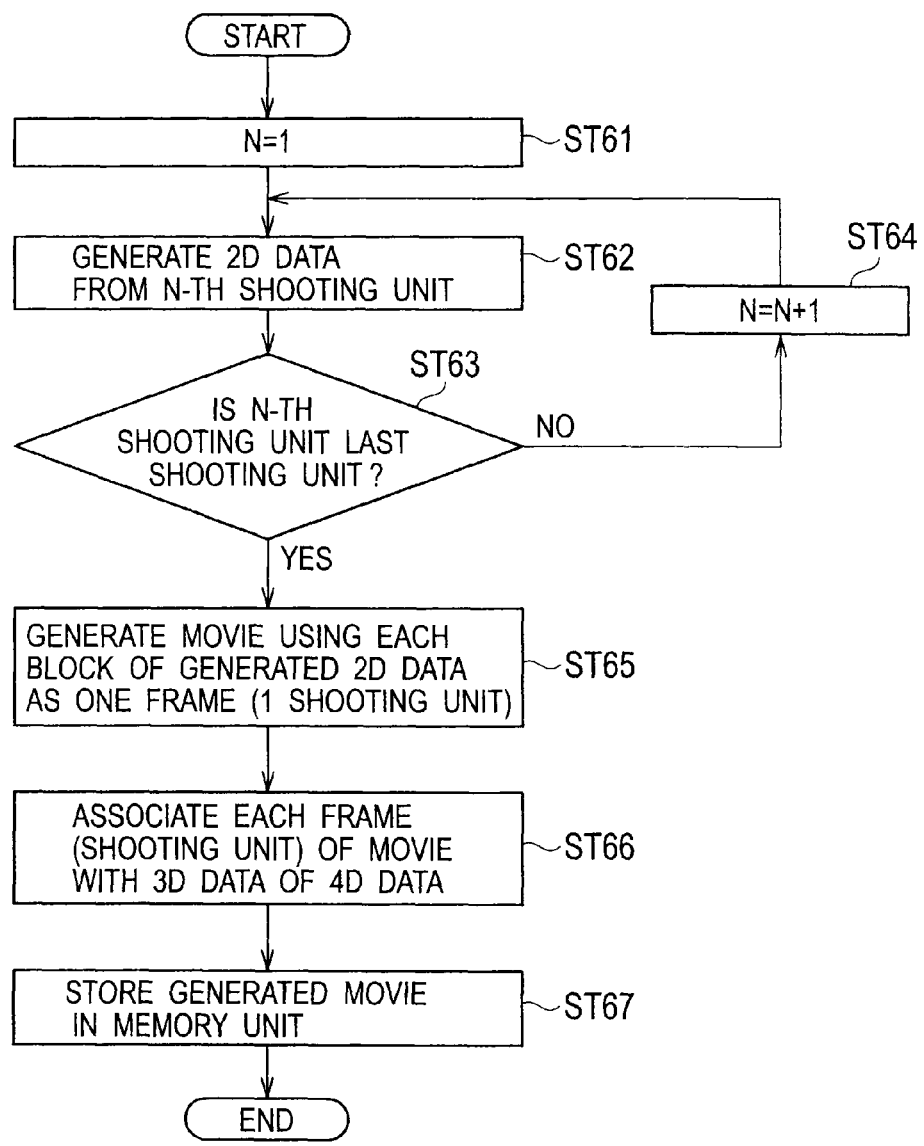
FIG. 5 is a flowchart showing a flow of generating the 2D movie data.

Next, description is given of the flow of generating the 4D image data based on the volume data taken by the medical image generation apparatus 1 and generating the 2D movie data from the 4D image data. FIG. 4 is a sequence diagram illustrating operations of the functions of the medical image generation apparatus 1. FIG. 5 is a flowchart showing the flow of generating the 2D movie data.

First, to collect the internal information of the object, the operator gives a shooting instruction through the input unit 1f of the medical image generation apparatus 1 (ST1). The CPU 1a which has received the instruction drives the drive unit 1l, such as the X-ray tube and X-ray detector detecting X rays, through the drive unit controller 1k to take images of the object (ST2). Herein, in the sequence diagram of FIG. 4, the drive unit 1l taking images of the object through the control by the drive unit controller 1k is collectively referred to as an image shooting unit. Moreover, in the sequence diagram of FIG. 4, the image generation unit 10 is representatively shown, but operations performed by the image generation unit 10 include processing practically performed by the CPU 1a of the medical image generation apparatus 1, for example, which are collectively shown.

When the image shooting unit finishes taking images of the object and collecting the internal information of the object (ST3), a signal indicating the end of taking images is sent to the CPU 1a, and the CPU 1a causes the memory unit 1i to store the obtained scanning data (ST4).

Next, based on the scanning data generated and stored in the memory unit 1i, the 4D image data is generated by the 4D image data generation unit 1m (ST5). For generating the 4D image data, first, 3D image data is generated from the scanning data.

Herein, the scanning data is obtained by taking images of a site to be examined several times or consecutively for a predetermined period of time. Accordingly, the collected scanning data includes scanning data blocks obtained at a plurality of different times. Specifically, a single block of scanning data is obtained at each shooting time and can be considered as a shooting unit. Using these blocks of scanning data obtained at different times, the 3D image data blocks are generated at individual times. Thereafter, based on the plurality of 3D image blocks, the 4D image data is generated. Specifically, the 3D image data blocks are organized in chronological order to form the 4D image data.

The 3D image data blocks may be individually generated several seconds after the beginning of the period of each shooting unit. Alternatively, in the case of a heart, for example, the 3D image data blocks may be individually generated for each phase, such as systole and diastole phases, and be organized in chronological order to form the 4D image data. Hereinafter, the time and phase are properly integrated as the shooting unit.

After the 4D image data is generated by the 4D image data generation unit 1m, the 2D movie data is generated by the image generation unit 10 (ST6). As described later, the operator sees the 2D movie data at the medical image display apparatus 3. Accordingly, for generating the 2D movie data, first, the conditions for specifying a proper position for the operator to browse a target site (an affected site) are set by the condition setting section 12.

Specifically, the conditions are set by using the 4D image data displayed at first, for example, among the 4D image data generated at ST5. Since the 4D image data includes the 3D image data blocks organized in chronological order, and the conditions are practically set by using the 3D image data block at a certain shooting unit constituting the 4D image data.

Examples of such conditions include rotation, cutoff, and a change in standpoint of the 4D image data for clearly displaying the disease of the site (affected site). The setting conditions are previously set and stored in the memory unit 1i. Accordingly, when the 4D image data is generated, the condition setting section 12 of the image generation unit 10 draws the conditions from the memory unit 1i, and the 4D image data (3D image data blocks) is processed based on the set conditions. The conditions may be set by the operator.

When processing of the 4D image data is finished, generation of the movie data is practically started. As shown in the flowchart of FIG. 5, first, the checking section 13 sets the shooting unit N of the target 4D image data to 1 (ST61). This is for sequentially generating the 2D image data blocks starting from the 3D image data block of a shooting unit of the processed 4D image data displayed at first. The shooting unit may be either the time or phase as described above, and the 2D image data at the Nth shooting unit is generated using the Nth 3D image data blocks (ST62).

Each 2D image data block is generated from the 3D image data block of individual shooting unit constituting the 4D image data by volume rendering (VR) or MPR. The generated 2D image data block is stored in the storage section 17 as the N-th 2D image data block. On the other hand, it is judged by the judgment section 15 whether the 2D image data blocks corresponding to the shooting unit numbers given to the generated 4D image data are already generated, that is, whether the N-th shooting unit is the last shooting unit (ST63). If the judgment section 15 judges that the 3D image data block which is the source of the 2D image data block to be generated is not the last shooting unit (No in ST63), an instruction is given to a counter to add 1 to N indicating the number in chronological order, and the 2D image data block is generated using the (N+1)th 3D image data block (ST62).

If the judgment section 15 judges that the N-th shooting unit is the last (Yes in ST63), it can be judged that the 2D image data blocks are generated using all of the 3D image data blocks. Accordingly, the judgment section 15 instructs the movie generation section 18 to generate movie data (ST65). The movie data is generated in the form of multi-frame DICOM image or Windows (registered trademark) standard AVI. The movie generation section 18 generates a movie using each generated 2D image data block as a single frame. As the first to N-th 2D image data blocks are already generated, N frames of the 2D image data blocks are sequentially arranged to generate the movie data. The operator thus reproduces and sees the generated movie data at the medical image display apparatus 3.

In some cases, the protocol of the movie data transmitted from the medical image generation apparatus 1 varies on the kind of the later-described medical image storage apparatus 2 storing the movie data. The network 4 may be connected to a plurality of the medical image storage apparatuses 2, and it is necessary to consider the protocol receivable by each medical image storage apparatus 2 at the time of generating the movie data. Moreover, for example, the medical image storage apparatuses 2 may be configured to individually store different medical images like: one of the medical image storage apparatuses 2 stores only the movie data while another one stores both the 4D image data and movie data.

The movie generation section 18 associates the generated movie data with the 3D image data blocks as the source of the movie data (ST66).

Specifically, for example, when the movie data is generated in the form of multiframe DICOM image, a link to the relevant 3D image data, that is, accompanying information, is stored in a DICOM tag which is configured to store the accompanying information concerning images. When the movie data is generated using Windows (registered trademark) standard AVI, a new object file is created, and link information to the relevant 3D image data is stored in such an external object file. It is therefore possible to identify the 3D image data associated with each frame of the movie. The link information only needs to be information capable of identifying the relevant 3D image data, such as a SOP instance unique identifier (UID) or a series instance UID in the case of DICOM. As for the location at which the relevant information is stored, the two types of locations are described above, but the relevant information may be stored at other locations if the movie and the relevant 3D image data are surely associated with each other.

Figure 6:
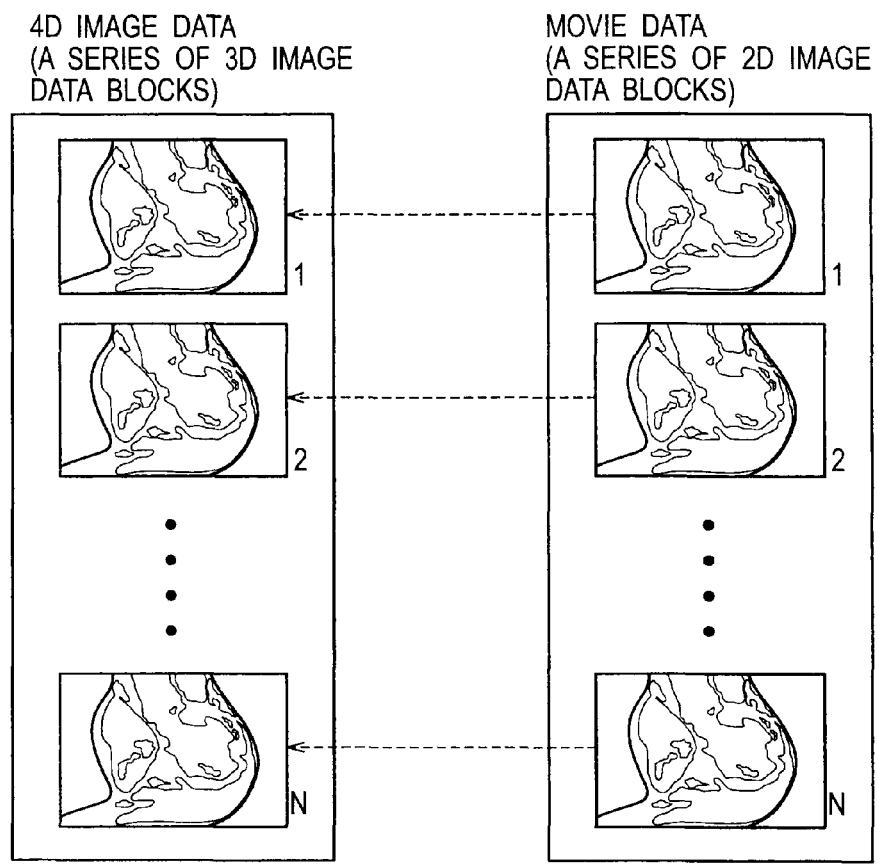
FIG. 6 is an explanatory view for explaining the concept of associating movie data with relevant 3D data in the embodiment of the present invention.

FIG. 6 is an explanatory view for illustrating the concept of associating the movie data and the 3D image data blocks. A series of 3D image data blocks of the first to N-th shooting units are conceptually shown on the left side of the drawing. In FIG. 6, these 3D image data blocks are organized in chronological order to form the 4D image data. On the right side of the drawing, the movie data generated by organizing the 2D image data blocks in chronological order is conceptually shown. Links between the 2D image data blocks constituting the movie data and the relevant 3D image data blocks are set. In FIG. 6, to show the relation between the both data blocks, dashed arrows extend from the movie data to the related 3D image data blocks.

The 3D image data blocks associated with the 2D image data blocks constituting the movie data are original 3D image data blocks generated based on the taken and collected scanning data which is used for generating the 4D image data. As described above, practically, the 3D image data blocks are processed at the step of processing the 4D image data. Accordingly, the processed 3D image data blocks may be used to generate the 2D image data blocks instead of the original 3D image data blocks. The movie data can be therefore associated with the processed 3D image data blocks.

The generated movie data, information concerning the 3D image data blocks associated with the 2D image data blocks constituting the movie data, and 4d image data are stored in the memory unit 1$i$ (ST67 and ST7). The 4D image data, which is stored in the memory unit 1$i$ at this step, may be once stored in the memory unit 1$i$, for example, between the generation of the 4D image data and generation of the movie data. Moreover, the movie data and 4D image data may be transmitted through the transmitter 19 and communication controller 1$h$ to the medical image storage apparatus 2 connected to the network 4 (ST8 and ST9). The medical image storage apparatus 2 stores the 4D image data and the movie data associated with the 3D image data blocks as the source of the 4D image data.

[Configuration and Function of Medical Image Display Apparatus]

Next, the configuration and functions of the medical image display apparatus 3 constituting the image display system S1 are described.

Figure 7:
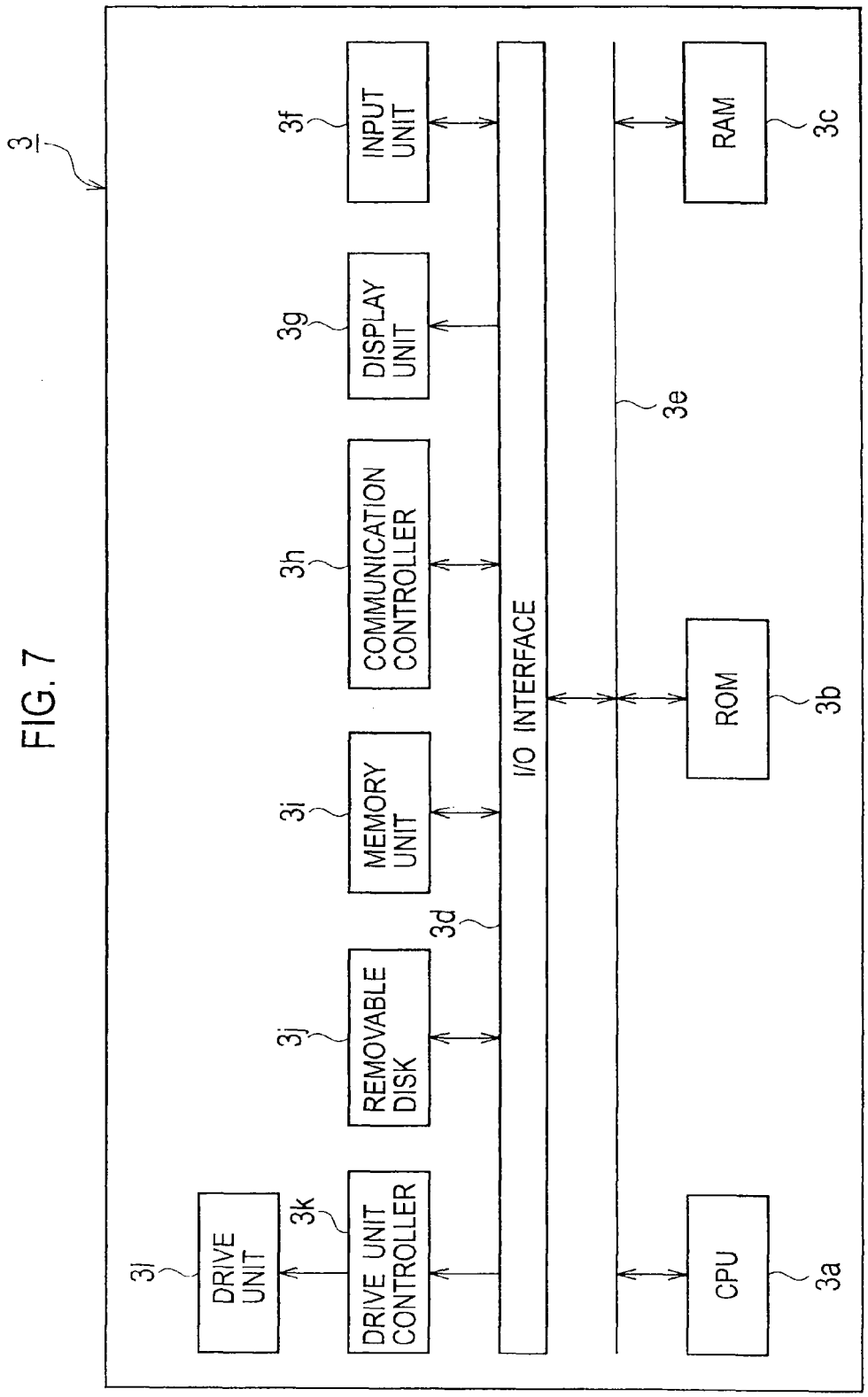
FIG. 7 is a block diagram showing the internal configuration of the medical image display apparatus of the embodiment of the present invention.

FIG. 7 is a block diagram showing the internal configuration of the medical image display apparatus 3 in the embodiment of the present invention. As the medical image display apparatus 3, for example, an information terminal such as a personal computer (PC) can be used. The medical image display apparatus 3 is not required to display 4D image data and only needs to have a performance adequate to display 3D image data.

The medical image display apparatus 3 includes a central processing unit (CPU) 3$a$, a read only memory (ROM) 3$b$, a random access memory (RAM) 3$c$, and an I/O interface 3$d$, which are connected to each other through a bus 3$e$. The I/O interface 3$d$ is connected to an input unit 3$f$, a display unit 3$g$, a communication controller 3$h$, a memory unit 3$i$, a removable disk 3$j$, and a drive unit controller 3$k$. The drive unit controller 3$i$ controls a drive unit 3$l$ driving a CD drive, for example.

The CPU 3$a$ reads a boot program to boot up the medical image display apparatus 3 from the ROM 3$b$ based on an input signal from the input unit 3$f$, executes the same, and reads out various types of operating systems stored in the memory unit 3$i$. The CPU 3$a$ controls various devices based on input signals received from other external devices not shown in FIG. 7 through the input unit 3$f$ or I/O interface 3$d$. Moreover, the CPU 3$a$ loads programs and data stored in the RAM 3$c$, memory unit 3$i$, and the like onto the RAM 3$c$. The CPU 3$a$ also serves as a processing unit implementing a series of processes including image display processing, data calculation and processing, and the like based on commands of the programs read from the RAM 3$c$.

The input unit 3$f$ is composed of input devices such as a keyboard and a mouse through which an operator of the medical image display apparatus 3 inputs various operations. The input unit 3$f$ creates the input signal based on the operation by the operator and sends the same to the CPU 3$a$ through the bus 3$e$. The 2D image data blocks constituting the movie data displayed on the display unit is specified through the input unit 3$f$. In this case, the input unit 3$f$ serves as a specifying unit which specifies the 2D image data.

The display unit 3$g$ is a liquid crystal display, for example. The display unit 3$g$ receives an output signal from the CPU 3$a$ through the bus 3$e$ and displays the movie data, 3D image data associated with the movie data, processing results of the CPU 3$a$, and the like.

The communication controller 3$h$ is a LAN card, a modem, or the like and allows the medical image display apparatus 3 to be connected to a communication network such as the Internet or LAN. Data exchanged with the communication network through the communication controller 3$h$ is exchanged with the CPU 3$a$ through the I/O interface 3$d$ and bus 3$e$ as input and output signals.

The memory unit 3$i$ is composed of a semiconductor or a magnetic disk and stores programs executed by the CPU 3$a$ and data.

The removable disk 3$j$ is an optical or flexible disk. Signals read and written into the removable disk 3$j$ by a disk drive are exchanged with the CPU 3$a$ through the I/O interface 3$d$ and bus 3$e$.

In the medical image display apparatus 3, the movie data and 3D image data are displayed as described above. The display is carried out by using an image display program stored in the memory unit 3$i$ or removable disk 3$j$. In this case, the stored program is loaded and executed by the CPU 3$a$, thus mounting the image display unit onto the medical image display apparatus 3.

Figure 8:
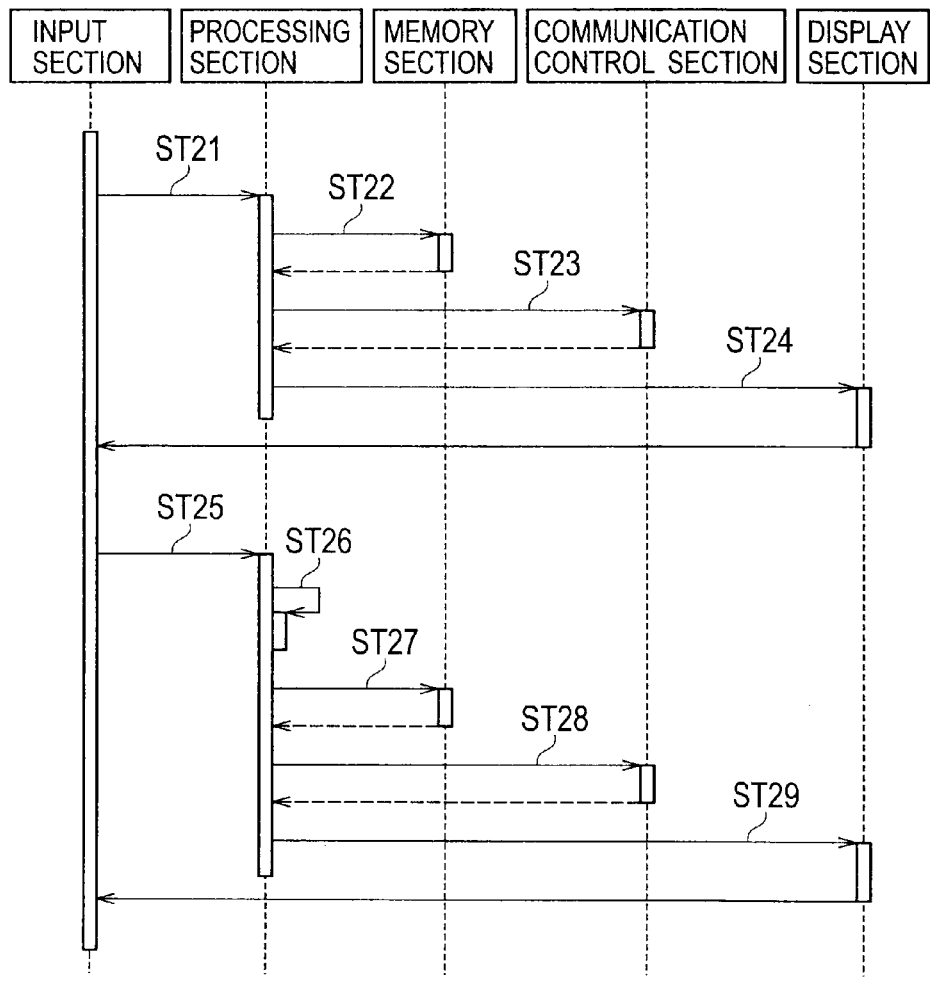
FIG. 8 is a sequence diagram showing a flow of displaying images in the medical image display apparatus together with operations of functions of the medical image display apparatus.

FIG. 8 is a sequence diagram showing a flow of displaying images in the medical image display apparatus 3. In FIG. 8, the CPU 3$a$, ROM 3$b$, and RAM 3$c$ are collectively shown as a "processing section" which performs processing concerning displaying images in the medical image display apparatus 3. The operator requests display of images of the object using the input unit 3$f$ (ST21). Herein, the image data requested by the operator may be any one of 4D image data, 3D image data, and movie data.

However, the medical image display apparatus 3 of the embodiment of the present invention does not have performance adequate to display 4D image data as described above. Moreover, as for the 3D image data, the plurality of 3D image data blocks generated at one scanning examination reaches a huge amount. Accordingly, it is difficult to display the huge amount of 3D image data and cause the operator to select proper 3D image data therefrom.

The processing section having received an instruction to display 4D image data instructs the memory unit 3$i$ to read a display program used for displaying the movie data related to the 4D image data to be displayed (ST22). The processing section also requests reading of the movie data from the medical image storage apparatus 2 through the communication controller 3$h$ (ST23). The display program is read from the memory unit 1*i* having received the instruction, and the movie data to be displayed is acquired from the medical imaged storage apparatus 2. The processing section displays the acquired movie data on the display unit 3*g* (ST24).

Figure 9:
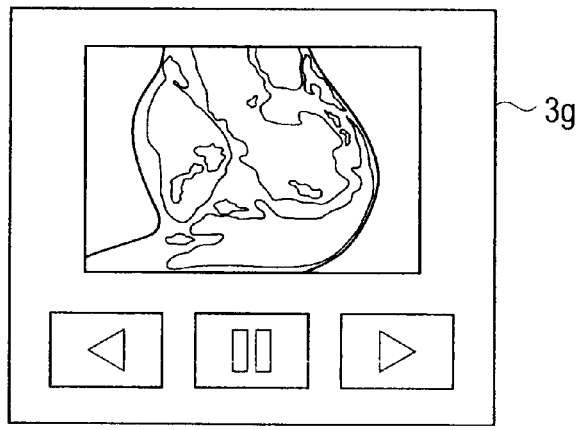
FIG. 9 is a screen example showing movie data displayed on a display unit.

FIG. 9 is a screen example showing the movie data displayed on the display unit 3*g*. In this screen example, the movie data is displayed on the display unit 3*g*, and under the display of the movie data, buttons to instruct reproduction of the movie data are provided. By operating these buttons properly, the operator can reproduce the movie data. Moreover, to search for an image of the necessary shooting unit, the operator operates the pause button to stop the reproduction of the movie data.

As shown in FIG. 9, operations can be carried out on the display unit 3*g* in this embodiment of the present invention. However, for example, the aforementioned operations can be also carried out using the input unit 3*f*. The screen example shown in FIG. 9 is no more than an example, and the screen design thereof, the way of reproducing the movie, and the like can be arbitrarily set.

When the operator finds out the 2D image of the necessary shooting unit among the movie data which is being reproduced, the operator presses a pause button to stop reproduction of the movie data. A certain shooting unit can be thus identified. When the operator clicks the movie data on the display unit 3*g* shown in FIG. 9, for example, the 3D image data of the identified shooting unit can be displayed. The request to display the 3D image data may be configured to be performed by clicking another button, for example.

When the movie data is clicked to make the request to display the 3D image data of the identified shooting unit (ST25), the processing section having received the request identifies the 3D image data block based on the information concerning the 3D image data associated with the displayed 2D image data block (ST26).

Figure 10:
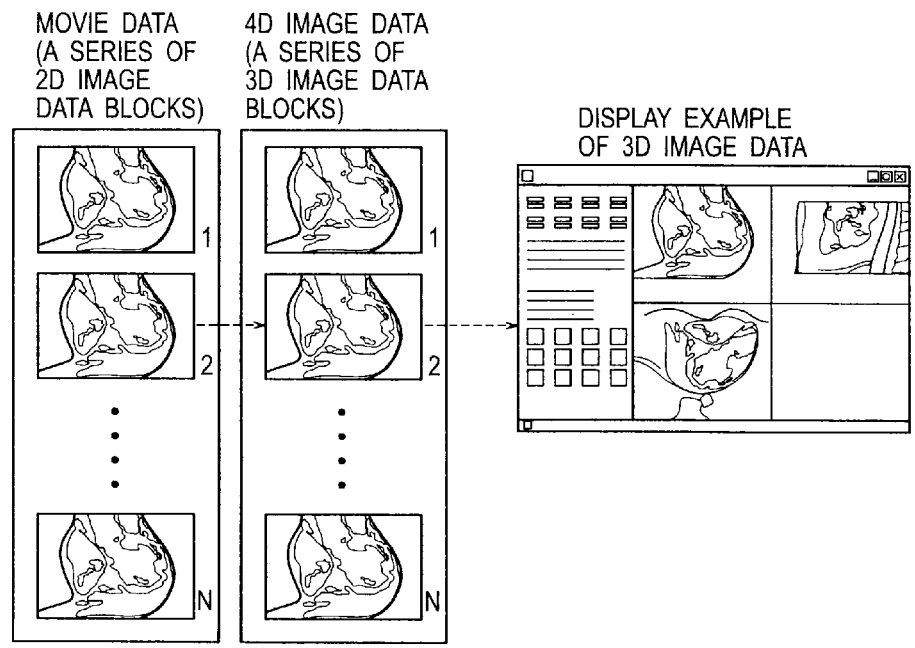
FIG. 10 is an explanatory view for explaining the concept in which an operator acquires relevant 3D image data from the movie data in the embodiment of the present invention.

FIG. 10 is an explanatory view for illustrating the concept when the operator acquires the relevant 3D image data block from the movie data. For example, when the operator brings the movie data on the display unit 3*g* shown in FIG. 9 to a pause and clicks the image which is being displayed, the second frame is identified among the 2D image data blocks displayed on the left side of FIG. 10. Based on the link information associated with the identified 2D image data block, the 3D image data block of the specified shooting unit is identified and is then read from the medical image storage apparatus 2. In the center of FIG. 10, the 4D image data, that is, the series of 3D image data blocks is shown. The 3D image data block associated with the identified 2D image data block is read based on the link information.

When the 3D image data block is identified, next, the processing section loads a 3D image data display program to display the 3D image data from the memory unit 3*i* (ST27). The processing unit requests reading of 3D image data from the medical image storage apparatus 2 through the communication controller 3*h* (ST28). The processing unit loads the 3D data display program from the instructed memory unit 3*i* and acquires the target 3D image data from the medical image storage apparatus 2. The processing section causes the acquired 3D image data to be displayed on the display unit 3*g* (ST29) (see the drawing on the right side of FIG. 10).

In FIG. 10, to clearly illustrate the relation between the 3D image data block of the shooting unit identified from the reproduced movie data and the 3D image data displayed on the display unit 3*g*, dashed arrows are shown therebetween. The screen example showing the 3D image data on the right side of FIG. 10 is no more than an example, and the screen may employ any design.

As described above, in the medical image generation apparatus 1, first, the 4D image data and movie data are generated from the generated 3D image data. On the other hand, in the medical image display apparatus 3, the movie data, which is smaller in data amount than the 4D image data, is reproduced. The operator specifies the necessary shooting unit from the displayed movie data, or specifies the 2D image data block constituting the displayed movie data. Thereafter, the 3D image data associated with the specified 2D movie data block is displayed. By performing such processes, it is possible to provide a medical image generation apparatus, medial image display apparatus, and medical image display system in which necessary image data can be selected and displayed from a large amount of image data with a simple operation regardless of the ability of the used medial image display apparatus.

In other words, according to the embodiment of the present invention, it is possible to remove complication and difficulties in displaying a list of a number of 3D image data blocks for example and selecting and displaying necessary image data therefrom and allow the operator to easily display the necessary image data by selecting and specifying the necessary image data while seeing the movie data which is being reproduced. Moreover, the 4D image data large in amount is processed into the movie data small in amount. In the medical image display apparatus, this movie is displayed, and necessary 3D image data is just selectively displayed. This enables display of necessary image data regardless of the performance of the medical image display apparatus connected to the network.

Second Embodiment

Next, a second embodiment of the present invention is described. In the second embodiment, the same constituent components as those described in the above first embodiment are given same reference numerals, and the description thereof is redundant and omitted.

In the aforementioned first embodiment, the medical image generation apparatus 1 generates the movie data based on 3D image data. However, in the second embodiment, the medical image storage apparatus 20 is configured to generate the movie data.

Figure 11:
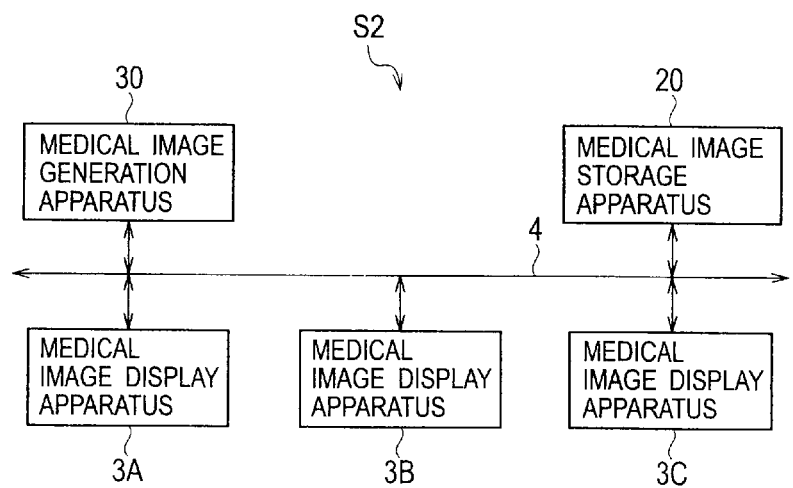
FIG. 11 is a block diagram showing the entire configuration of an image display system according to a second embodiment of the present invention.

FIG. 11 is a block diagram showing the entire configuration of an image display system S2 according to the second embodiment of the present invention. The image display system S2 includes a medical image generation apparatus 30, the medical image storage apparatus 20, and the medical image display apparatus 3, which are connected to the network 4. The medical image generation apparatus 30 takes images of an object to acquire image information. The medical image storage apparatus 20 stores the image information acquired by the medical image generation apparatus 30 and generates 2D movie data from a plurality of time-series 3D image data blocks. The medical image display apparatus 3 can display the movie data generated by the medical image storage apparatus 20.

The medical image storage apparatus 20 may be configured to store not only the image data acquired by the medical image generation apparatus 30 but also image data read from memory media such as optical disks.

Figure 12:
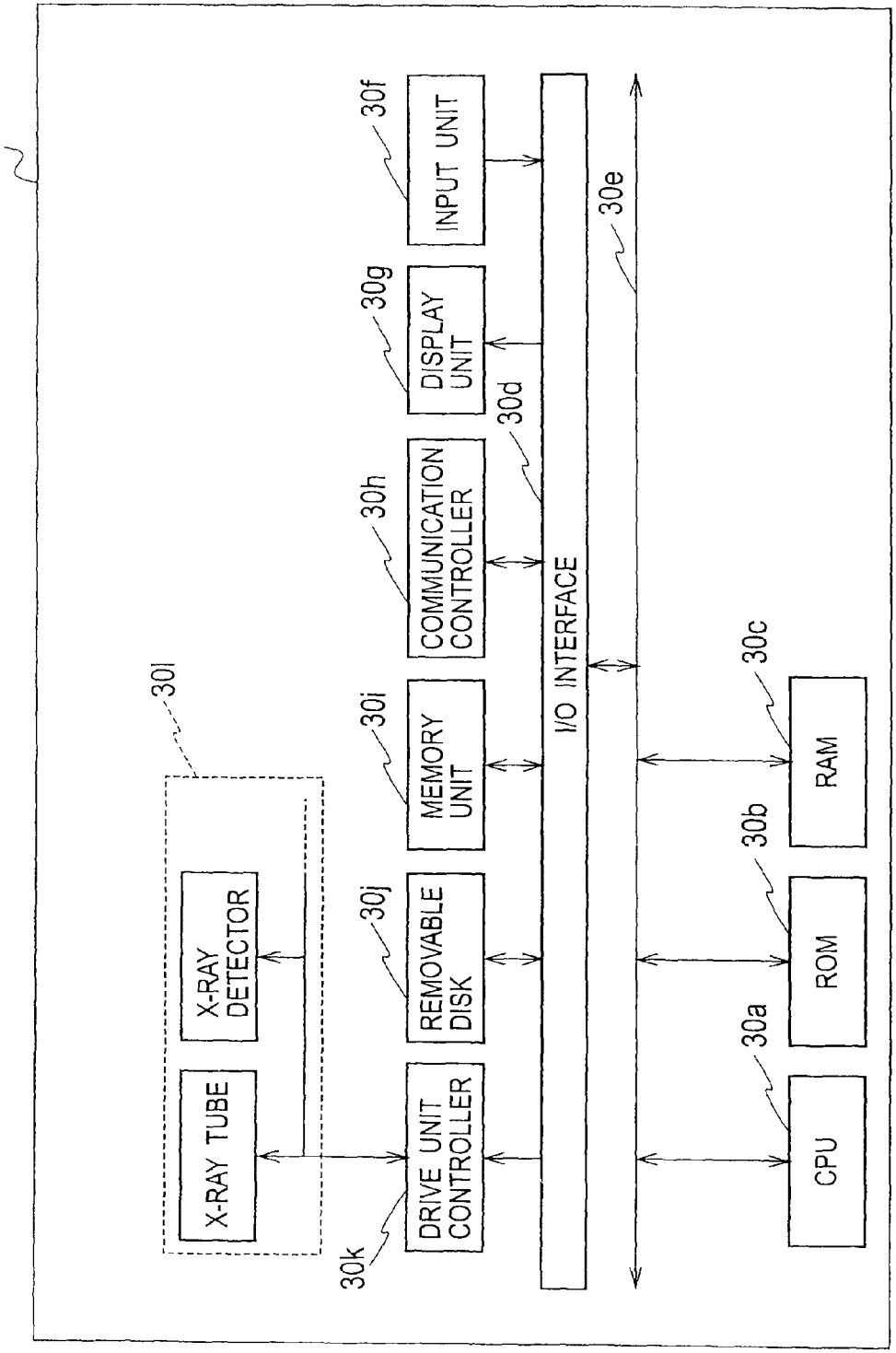
FIG. 12 is a block diagram showing the internal configuration of a medical image generation apparatus according to the second embodiment of the present invention.

FIG. 12 is a block diagram showing the internal configuration of the medical image generation apparatus 30. The difference between the medical image generation apparatuses 1 and 30 of the first and second embodiments is that the medical image generation apparatus 30 of the second embodiment only acquires the image information indicating the inside of the object and does not generate movie data. Accordingly, the medical image generation apparatus 30 does not include the 4D image data generation unit 1m and image generation unit 10, which are provided for the medical image generation apparatus 1. These 4D image data generation unit and image generation unit are provided for the medical image storage apparatus 20. The other configurations of the medical image storage apparatus 20 are the same as those of the medical image generation apparatus 1, and the description thereof is omitted.

Figure 13:
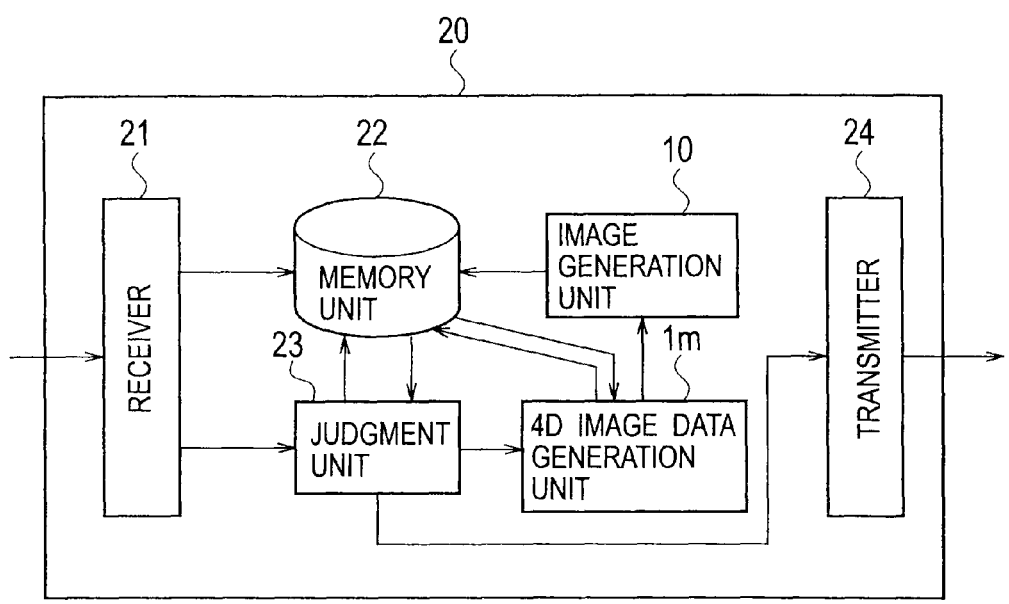
FIG. 13 is a block diagram showing the internal configuration of a medical image storage apparatus according to the second embodiment of the present invention.

FIG. 13 is a block diagram showing the internal configuration of the medical image storage apparatus 20. The medical image storage apparatus 20 includes: a memory unit 22 storing the image information acquired (taken) by the medical image generation apparatus 30; a judgment unit 23 extracting necessary movie data from the memory unit 22 and the like and sending the same based upon an instruction from the medical image display apparatus 3; and 4D image data generation unit 1m and image generation unit 10 generating movie data upon an instruction from the judgment unit 23. The medical image storage apparatus 20 certainly includes a receiver and transmitter 24 which receives and transmits information, respectively.

The memory unit 22 stores the image information transmitted from the medical image generation apparatus 30 and also stores movie data generated in the image generation unit 10 and information on links to relevant 3D image data.

The judgment unit 23 receives a request to read movie data transmitted through the communication controller 3h of the medical image display apparatus 3 (see ST23). The judgment unit 23 acquires the requested movie data from the memory unit 22 and sends the same through the transmitter 24 to the medical image display apparatus 3 as the source of the request.

The functions concerning the 4D image data generation unit 1m and image generation unit 10 are as described in the first embodiment. According to the second embodiment, in the medical image storage apparatus 20, based on the image information supplied from the medical image generation apparatus 30, the 4D image data generation unit 1m generates the 4D image data, and the image generation unit 10 generates movie data and sets a link to the 3D image data related thereto.

One of the methods for setting the link to the 3D image data related to the movie data is storing the link in a DICOM tag (accompanying information). Alternatively, the link may be stored in an object file newly created. Moreover, in the medical image storage apparatus 20, the accompanying information of the stored image data may be stored in the memory unit 22 as a database. In this case, the accompanying information of the links to the 3D image data blocks related to the 2D image data blocks may be stored in the database. When there is a request to read the movie data, it is therefore possible to simultaneously read the link (accompanying information) to the related 3D image data.

As for the location at which the relevant information is stored, three different locations are described above as examples thereof, but the relevant information may be stored at other locations if the 2D image data blocks constituting the movie data and the 3D image data blocks related thereto are surely associated with each other.

By employing the aforementioned configuration, it is possible to provide the same effect as the first embodiment only by extending the functions of the medical image storage apparatus 20 without providing high performance enough to generate movie data for the medical image generation apparatus 30.

The present invention is not limited to the aforementioned embodiments, and the constituent elements can be modified and embodied without departing from the spirit of the invention. Moreover, the plurality of constituent elements disclosed in the above embodiments can be properly combined to form various inventions. For example, some constituent elements may be removed from all of the constituent elements shown in the embodiments. Furthermore, the constituent elements of different embodiments may be properly combined.

What is claimed is:

1. A medical image display system, comprising:
   a medical image generation apparatus, including:
   a four-dimensional image data generation circuit generating four-dimensional image data composed of a plurality of three-dimensional image data blocks each having information indicating a number in chronological order of the three-dimensional image data blocks by using image information acquired by taking images of an object;
   a memory storing the four-dimensional image data generated by the four-dimensional image data generation unit; and
   an image generation circuit generating movie data composed of a plurality of two-dimensional image data blocks generated from the plurality of three-dimensional image data blocks constituting the four-dimensional image data stored in the memory, and generating relevant information associating each of the two-dimensional image data blocks constituting the movie data with one of the three-dimensional image data blocks which is a source of the blocks of two-dimensional image data; and
   a medical image display apparatus connected to the four-dimensional image data generation circuit, the memory, and the image generation circuit through a network, and displaying the two-dimensional image data blocks and the three-dimensional image data blocks,
   wherein when one of the two-dimensional image data blocks is identified in the movie data at the medical image display apparatus, the three-dimensional image data block corresponding to the identified two-dimensional image data block is read based on the relevant information through the network, and the read three-dimensional image data block is displayed on the medical image display apparatus.

2. The medical image display system according to claim 1, wherein the relevant information is stored as attendant information of the two-dimensional image data.

3. The medical image display system according to claim 1, wherein the relevant information is stored in an object file associated with each block of two-dimensional image data.

4. A medical image display system, comprising:
   a medical image generation apparatus including
   a four-dimensional image data generation circuit generating four-dimensional image data composed of a plurality of three-dimensional image data blocks each having a number in chronological order of the three-dimensional image data blocks using image information acquired by taking images of an object;
   an image generation circuit generating movie data composed of a plurality of two-dimensional image data blocks generated from the three-dimensional image data blocks constituting the four-dimensional image data and generating relevant information associating each of the two-dimensional image data blocks with one of the three dimensional image data blocks which is a source of the two-dimensional image data blocks; and a medical image display apparatus connected to the four-dimensional image data generation circuit and the image generation circuit through a network, and displaying the two-dimensional image data blocks and the three-dimensional image data blocks, wherein when one of the two-dimensional image data blocks is identified on the movie data, the three-dimensional image data block corresponding to the identified two-dimensional image data block is read based on the relevant information through the network, and the read three-dimensional block is displayed on the medical image display apparatus.

* * * * *